United States Patent [19]
Knutson et al.

[11] Patent Number: 5,529,991
[45] Date of Patent: Jun. 25, 1996

[54] ORAL 1α-HYDROXYPREVITAMIN D

[75] Inventors: Joyce C. Knutson, Madison; Charles R. Valliere, Waunakee; Charles W. Bishop, Verona, all of Wis.

[73] Assignee: Lunar Corporation, Madison, Wis.

[21] Appl. No.: 196,116

[22] Filed: Feb. 22, 1994

Related U.S. Application Data

[63] Continuation-in-part of Ser. No. 901,886, filed as PCT/US93/05961, Jun. 22, 1993, published as WO94/00128, Jan. 6, 1994, abandoned.

[51] Int. Cl.⁶ .................................................. A01N 45/00
[52] U.S. Cl. .................................................. 514/170
[58] Field of Search ................................. 514/170

[56] References Cited

U.S. PATENT DOCUMENTS

| | | |
|---|---|---|
| 2,216,719 | 10/1940 | Boer . |
| 2,434,015 | 1/1948 | Rosenberg et al. . |
| 4,230,701 | 10/1980 | Holick et al. . |
| 4,335,120 | 6/1982 | Holick et al. . |
| 4,505,906 | 3/1985 | DeLuca et al. . |
| 4,539,153 | 9/1985 | Vandewalle et al. . |
| 4,684,524 | 8/1987 | Echenhoff et al. ............ 424/469 |
| 4,728,643 | 3/1988 | Holick et al. . |
| 5,013,728 | 5/1991 | Grodberg . |

FOREIGN PATENT DOCUMENTS

| | | |
|---|---|---|
| 649802 | 2/1994 | Australia . |
| 650286 | 6/1994 | Australia . |
| 0070588 | 1/1983 | European Pat. Off. . |
| 0215956 | 4/1987 | European Pat. Off. . |
| 0306236 | 8/1989 | European Pat. Off. . |
| WO84/04527 | 5/1984 | WIPO . |
| WO90/09179 | 8/1990 | WIPO . |
| WO92/09271 | 6/1992 | WIPO . |

OTHER PUBLICATIONS

CA 116:254522 1991.
CA 115:278633 1990.
CA 110:107718 1988.
CA 116:75862 1991.
Patent Abstracts of Japan, vol. 8, No. 93 (C–220) (1530) 27 Apr. 1984 document member of JP patent family JP,A, 59 010562 (TEIJIN K.K.) 20 Jan. 1984. (English Abstract only.).
*Transactions of the Association of American Physicians*, vol. XCII, 1979, pp. 54–63, M. F. Holick, S. C. McNeill, J. A. MacLaughlin, S. A. Holick, M. B. Clark and J. T. Potts, Jr., "Physiologic Implications of the Formation of Previtamin D in Skin".
*Chemical Abstracts*, vol. 110, No. 10, 1989, Columbus, Ohio, Abstract No. 84136v, M. Takahashi, H. Mochizuki, "Enteric–Soluble Capsule Base Composed of Poly(Ethylene Glycol) or Its Substitutes and Cellulose Acetate Phthalate or Hydroxypropyl Methyl Cellulose Phthalate".
*Harrison's Principles of Internal Medicine*: Part Eleven, "Disorders of Bone & Mineral Metabolism," Chapter 335, E. Brauwald et al., (eds.) McGraw–Hill, New York (1987) pp. 1860–1865.
M. L. Curtin and W. H. Okamura, *J. Am. Chem. Soc.*, vol. 113 (1991) pp. 6958–6966.

*Primary Examiner*—Paul J. Killos
*Attorney, Agent, or Firm*—Teresa J. Welch; Stroud, Stroud, Willink, Thompson & Howard

[57] ABSTRACT

This invention relates to delayed and sustained release oral medicaments and, more specifically, to delayed and sustained release activated vitamin D, oral medicament.

22 Claims, No Drawings

ORAL 1α-HYDROXYPREVITAMIN D

The application is a continuation-in-part of Ser. No. 07/901,886 filed on Jun. 22, 1992, abandoned, and a 371 of PCT/US93/05961 filed Jun. 22, 1993.

BACKGROUND OF THE INVENTION

Vitamin D is known to be important in the regulation of calcium metabolism in animals and man. See, *Harrison's Principals of Internal Medicine*: Part Eleven "Disorders of Bone and Mineral Metabolism," Chapter 335, E. Braunwald et al., (eds.), McGraw-Hill, New York (1987) pp. 1860–1865.

Vitamin $D_3$ is synthesized endogenously in the skin of animals and man from 7-dehydrocholesterol by an ultraviolet-mediated photochemical reaction which breaks the B ring of the 7-dehydrocholesterol between carbon-4 and carbon-9 to form previtamin $D_3$. The triene previtamin $D_3$ is unstable and over time thermally converts to vitamin $D_3$. At normal body temperature an equilibrium exists between previtamin $D_3$ and vitamin $D_3$, as seen below.

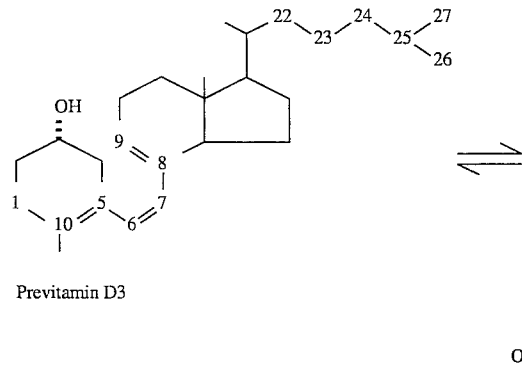

Previtamin D3

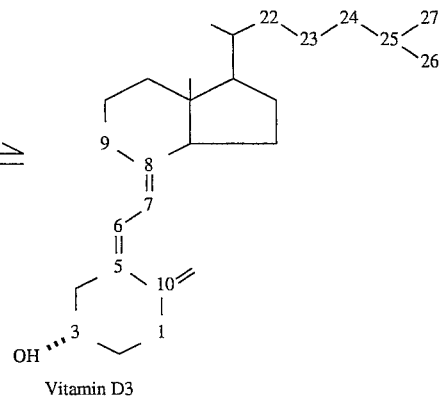

Vitamin D3

As vitamin $D_3$ is further metabolized in vivo this equilibrium shifts to the vitamin $D_3$ form. It is known that vitamin $D_3$ must be hydroxylated at the carbon-1 and the carbon-25 position before it is activated, i.e., before it will produce a biological response. A similar metabolism appears to be required to activate the other forms of vitamin D, e.g., vitamin $D_2$ and vitamin $D_4$. As is generally understood and used herein, the term "vitamin D" is intended to include vitamins $D_3$, $D_2$, and $D_4$. The term "activated vitamin D," as used herein, is intended to refer to vitamin D which has been hydroxylated in at least the carbon-1 position of the A ring, e.g., 1α-hydroxyvitamin $D_3$.

Functionally, vitamin D is more appropriately considered a hormone than a vitamin. When activated, vitamin D interacts with a vitamin D receptor protein and this interaction ultimately results in some form of biological response. For example, 1α,25-dihydroxyvitamin $D_3$ is known to be a potent stimulator of calcium absorption from the intestine, such absorption is mediated by the interaction of the 1α,25-dihydroxyvitamin $D_3$ molecule and the vitamin D receptor protein located in the epithelial cells (enterocytes) which line the intestine.

In recent years it has become evident that the vitamin D receptor protein is widely distributed in the bodies of animals and man. Thus, it is not surprising that in addition to influencing calcium homeostasis, activated vitamin D has been implicated in osteogenesis, modulation of immune response, modulation of the process of insulin secretion by the pancreatic B cell, muscle cell function and the differentiation and growth of epidermal and hemopoietic tissues.

Such a wide range of biological actions suggests that the activated forms of vitamin D compounds should be valuable therapeutic agents for a wide range of maladies such as metabolic bone disease, osteoporosis, psoriasis, psoriatic arthritis, colon, prostrate and breast cancer, and HIV infection. Unfortunately, when these agents are administered orally, the potent stimulation of calcium absorption by activated vitamin D can readily cause a dangerous hypercalcemia before the desired therapeutic response is obtained. For this reason, the activated vitamin D compounds are generally considered to have a low therapeutic to toxic ratio or low therapeutic index. Additionally, the presently known oral formulations when administered produce an unphysiologically rapid increase in the blood level of both calcium and activated vitamin D hormone followed by an almost as rapid decrease in the blood level of activated vitamin D hormone. Such rapid peaks and valleys of either the blood calcium or the activated vitamin D hormone are undesirable and perhaps harmful.

Recognizing the great potential of activated vitamin D as a therapeutic agent, alternative routes of administration which would allow higher sustained blood levels to be achieved and yet avoid the toxicity problems presented by the oral dosage form have been sought. To this end, an injectable form of 1α,25-dihydroxyvitamin $D_3$ has been developed by Abbott Laboratories and is marketed under the trade name Calcijex for the management of hypocalcemia in patients undergoing chronic renal dialysis. Topical and transdermal forms of the drug have also been suggested by Holick, U.S. Pat. No. 4,230,701.

These alternative routes of administration, however, lack the convenience and the reliability of an oral dosage form and, to that extent, have diminished the practicality and attractiveness of activated vitamin D compounds as therapeutic agents. What is needed, is an oral dosage form which produces a more physiological sustained increase in the blood level of activated vitamin D and has a more acceptable therapeutic index than is presently possible with heretofore known oral formulations of activated vitamin D.

SUMMARY OF THE INVENTION

The present invention responds specifically to the long-felt need heretofore unmet by the prior art and especially with a view to overcoming the inherent inadequacies of presently known oral vitamin D formulations. The present invention provides a delayed and sustained release, activated vitamin D, oral medicament.

In one embodiment, the invention provides a pharmaceutical composition and method for increasing activated vitamin D blood level by administering orally a compound of formula (I) or (II) as defined hereinbelow. The compounds of formulas (I) and (II) include 1α-hydroxyprevitamin D and 1α,25-dihydroxyprevitamin D.

In accordance with this embodiment of the invention, it has been unexpectedly found that orally administered 1α,25-dihydroxyprevitamin D produces a sustained increase in the blood level of 1α,25-dihydroxyvitamin D and has a higher therapeutic index than does orally administered 1α,25-dihydroxyvitamin D. The increased activated vitamin D blood level is achieved with significantly less hypercalcemia than that resulting from oral dosing of the 1α,25-dihydroxyvitamin D.

This embodiment of present invention is carried out by manufacturing 1α-hydroxyprevitamin D so that the 1α-hydroxyprevitamin D form remains relatively stable at room temperature. The 1α-hydroxyprevitamin D is then administered to an animal or human being in an oral dosage formulation. As the 1α-hydroxyprevitamin D is released from the oral dosage formulation, it is absorbed from the intestine into the blood. In the 1α-hydroxyprevitamin D form, the compound is inactive (i.e., does not bind to the vitamin D receptor protein) and does not stimulate intestinal calcium absorption. As the 1α-hydroxyprevitamin D is warmed by the core temperature of the animal or human being, it is thermally converted to the corresponding activated vitamin D. The thermal conversion to the active form takes a sufficiently long period of time such that most of this conversion occurs in the time period after the 1α-hydroxyprevitamin D has been absorbed into the blood stream of the animal or human being. Thus, the 1α-hydroxyprevitamin D oral dosage formulation produces a greater sustained blood level of the corresponding activated vitamin D with significantly less stimulation of intestinal calcium absorption than is obtained by administering orally the corresponding activated vitamin D itself.

In another embodiment of the present invention, activated vitamin D is incorporated in sustained release formulation suitable for administration orally. Ideally, the formulation has an enteric coating which is resistant to disintegration in gastric juice. The enteric coating covers a matrix which binds the active form of the vitamin D for gradual release once the enteric coating has dissolved. The enteric coating is designed to dissolve at a pH above that which is found in the stomach and proximal part of the small intestine.

In accordance with this embodiment of the invention, it has been found that when the enteric-coated, sustained release formulation of activated vitamin D is administered orally to an animal or human, it produces a sustained increase in the blood level of activated vitamin D and has a higher therapeutic index than does the heretofore known oral formulations of activated vitamin D.

The invention is carried out by formulating the activated vitamin D preparation so that it is bound in a matrix which provides a sustained release when exposed to the contents of the intestine. The activated vitamin D containing matrix is then covered with an enteric coating that is resistant to disintegration in gastric juices. The enteric coated, sustained release formulation of activated vitamin D (hereafter referred to a "DSR activated D") is then administered orally to the animal or human. As the DSR activated D of the invention travels past the proximal portion of the small intestine, the enteric coating dissolves. The active vitamin D containing matrix is exposed to intestinal fluids and activated vitamin D is gradually released over a sustained period of time and absorbed into the blood stream. Since the major portion of activated vitamin D is absorbed at a point beyond the proximal portion of the small intestine, a reduced stimulation of calcium uptake from the intestine occurs. This reduces the risk of hypercalcemia and hypercalciuria thus increasing the therapeutic window. The gradual release also allows a greater sustained level of activated vitamin D compound in the serum to be obtained.

In a third embodiment of the present invention the first and second embodiments are combined to provide a delayed and sustained release oral medicament of activated previtamin D (hereafter referred to as "DSR activated pre D") or of a combination of activated previtamin D and activated vitamin D (hereafter referred to as "DSR activated pre D and D"). This embodiment of the invention comprises one or more of the compounds of formulas (I), (II), (III), and/or (IV) contained in an enteric coated, sustained release formulation suitable for oral administration.

The foregoing and other advantages of the present invention are realized in one aspect thereof in a method for increasing the blood level of activated vitamin D in an animal or human being by administering orally an effective amount of 1α-hydroxyprevitamin D, or an effective amount of activated vitamin D contained in the DSR activated D formulation of the invention or a combination thereof. A preferred embodiment of 1α-hydroxyprevitamin D is 1α,25-dihydroxyprevitamin $D_3$ and a preferred embodiment of activated vitamin D is 1α,25-dihydroxyvitamin $D_3$.

In another aspect, the invention is a method of increasing blood level of activated vitamin D for a sustained period of time, typically greater than four hours.

In yet another aspect, the invention is a method for treating osteoporosis by administering orally an effective amount of 1α-hydroxyprevitamin D, or an effective amount of activated vitamin D contained in the DSR activated D formulation or a combination thereof.

In a further aspect, the invention is a method of treating psoriasis by orally administering an effective amount of 1α-hydroxyprevitamin D, or an effective amount of active vitamin D contained in the DSR activated D formulation or a combination thereof.

The compounds of formulas (I), (II), (III) and/or (IV) are provided in pharmaceutical compositions in combination with a pharmaceutically acceptable excipient. These compositions constitute another aspect of the invention. Preferred compositions include compounds of formula (II) which include 1α,25-dihydroxyprevitamin $D_3$, 1α,25-dihydroxyprevitamin $D_2$, and 1α,25-dihydroxyprevitamin $D_4$ and of formula (IV) which include 1α,25-dihydroxyvitamin $D_3$, 1α,25-dihydroxyvitamin $D_2$, and 1α,25-dihydroxyvitamin $D_4$.

Other advantages and a fuller appreciation of the specific adaptations, compositional variations and chemical and physical attributes of this invention will be gained upon examination of the detailed description and appended claims.

BRIEF DESCRIPTION OF THE DRAWING

The preferred exemplary embodiment of the present invention will hereinafter be described in conjunction with the appended drawing wherein like designations refer to like elements throughout and in which:

FIG. 1 is a graph which illustrates the time course of relative blood levels of active vitamin D after oral administration of 1α,25-(OH)$_2$D$_3$ in a delayed sustained release formulation and vehicle only.

DETAILED DESCRIPTION

The preferred embodiments of the present invention relate broadly to therapeutic methods for ameliorating certain medical conditions by improving blood levels of activated vitamin D, and specifically, to improving such levels for a sustained period of time with significantly less resultant hypercalcemia and hypercalciuria by administering orally the formulations described below.

First Embodiment

In accordance with the first embodiment of the present invention, it has been found that when substantially pure 1α-hydroxyprevitamin D is administered orally, it produces a greater sustained increase in the blood level of activated vitamin D and significantly less hypercalcemia and hypercalciuria than the same amount of activated vitamin D administered orally in previously known formulations. As used herein, the term "substantially pure" means at least 85% pure 1α-hydroxyprevitamin D. The term "sustained" as used herein means a blood level which remains relatively constant (i.e., ±10 pg/ml or ±10% of the mean value) for a period greater than a defined period.

The 1α-hydroxyprevitamin D of this embodiment of the present invention has the general formula (I):

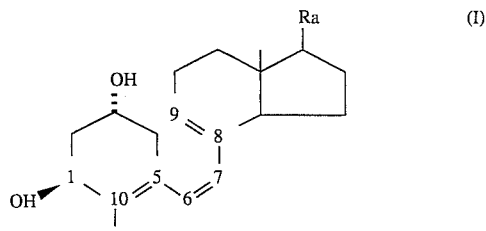

wherein R$_a$ is a side chain having at least 7 carbon atoms, and can be branched or unbranched, saturated or unsaturated, hetero-substituted or nonhetero-substituted, cyclic or noncyclic and wherein the thermal isomer (or vitamin form) of the 1α-hydroxyprevitamin D of the general formula increases the serum calcium of the vitamin D deficient rat as determined by standard techniques used by biochemists in the vitamin D area.

Among the preferred 1α-hydroxyprevitamin D of this embodiment of the present invention are those having the formula (II):

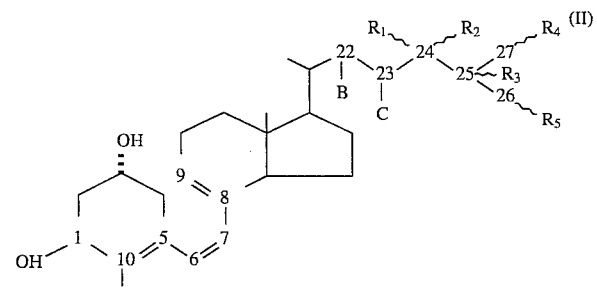

wherein B and C are either hydrogen or a carbon to carbon bond forming a double bond between C22 and C23; R$_1$, R$_3$, R$_4$ and R$_5$ are each independently hydrogen, hydroxy, lower alkyl, O-lower alkyl, O-lower acyl, O-aromatic acyl or flouro; and R$_2$ is hydrogen or lower alkyl. Most preferred among the compounds of formula (II), i.e., most preferred 1α-hydroxyprevitamin D compounds, are:

1α,25-dihydroxy-precholecalciferol [1α,25-(OH)$_2$preD$_3$];
1α,24,25-trihydroxy-precholecalciferol [1,α24,25-(OH)$_3$preD$_3$];
1α-hydroxy-precholecalciferol[1α-(OH)preD$_3$];
1α,24-dihydroxy-precholecalciferol[1,α24-(OH)$_2$preD$_3$];
1α,24-dihydroxy-25-fluoro-precholecalciferol[1,α24-(OH)$_2$25FpreD$_3$];
1α,25-dihydroxy-preergocalciferol[1,α25-(OH)$_2$preD$_2$];
1α,24,25-trihydroxy-preergocalciferol[1,α24,25-(OH)$_3$preD$_2$];
1α-hydroxy-preergocalciferol[1α-(OH)preD$_2$];
1α,24-dihydroxy-preergocalciferol[1,α24-(OH)$_2$preD$_2$];
1α,24-dihydroxy-25-fluoro-preergocalciferol[1α,24-(OH)$_2$25FpreD$_2$];
1α,25-dihydroxy-previtamin D$_4$[1α,25-(OH)$_2$preD$_4$];
1α,24,25-trihydroxy-previtamin D$_4$[1α,24,25-(OH)$_3$preD$_4$];
1α-hydroxy-previtamin D$_4$[1α-(OH)preD$_4$];
1α,24-dihydroxy-previtamin D$_4$[1α,24-(OH)$_2$preD$_4$]; and
1α,24-dihydroxy-25-fluoro-previtamin D$_4$1α,24-(OH)$_2$25FpreD$_4$].

In the formulae shown in this specification and in the claims, a wavy line to substituent X indicates that the substituent can be stereoisomeric alternate forms. Wherever in this specification and in the claims the word "lower" is used as a modifier of alkyl or acyl, it is intended to identify a hydrocarbon chain having from about 1 to 4 carbon atoms which has either a straight chain or branched chain configuration. Specific examples of such hydrocarbon chains are: methyl, ethyl, propyl, butyl, isobutyl or t-butyl, and formyl, acetyl, propionyl, or butyryl. The term "aromatic acyl" as used herein and in the claims is meant to identify a benzoyl group or a substituted benzoyl group such as nitrobenzoyl or dinitrobenzoyl.

In a preferred embodiment, the compounds of formulas (I) or (II) are provided in a crystalline form. 1α-Hydroxyprevitamin D in the crystalline form remains quite stable at room temperature with minimal conversion to the 1α-hydroxyvitamin D form. The compounds of formulas (I) or (II), i.e., 1α-hydroxyprevitamin D, can be readily manufactured in crystalline form according to the procedure described in Vandewalle, U.S. Pat. No. 4,539,153.

The pharmacologically active compounds of this embodiment can be processed in accordance with conventional methods of pharmacy to produce medicinal agents for administration to patients, e.g., mammals, including human beings. For example, dosage forms of the compounds of formulas (I) or (II) with conventional excipients, include admixtures suitable for oral administration. Dosage forms of the 1α-hydroxyprevitamin D can be combined with any nontoxic pharmaceutically acceptable carrier, such as cornstarch, lactose, or sucrose, which does not deleteriously react with the active compounds. The formulation can be produced in tablet, capsule, powders, troches and lozenges. Whatever method of formulation is used, care should be taken to avoid extended exposure to solvents and heat as under such conditions there will be a tendency for a portion 1α-hydroxyprevitamin D to convert to the 1α-hydroxyvitamin D form. Because heat and dissolution are preferably avoided, the preferred method of tablet formulation is the method known as dry granulation.

The 1α-hydroxyprevitamin D is administered to the animal or human in oral dosage formulation. As the 1α-hydroxyprevitamin D is released from the oral dosage formulation, it is absorbed from the intestine into the blood. 1α-Hydroxyprevitamin D does not interact with the vitamin D receptor protein of the enterocytes and, therefore, does not stimulate intestinal calcium absorption.

It is also known that the binding of activated vitamin D with the vitamin D receptor protein of the enterocyte induces the release of enzymes which degrade a significant portion of the unbound activated vitamin D present in the intestine. Such degradation decreases the amount of activated vitamin D available for absorption into the blood stream. Since 1α-hydroxyprevitamin D does not bind with the vitamin D receptor protein there is no enzyme induction. Thus, less degradation occurs in the intestine and a greater amount is available for absorption into the blood stream than is the case with the corresponding activated vitamin D.

As the 1α-hydroxyprevitamin D is warmed by the core temperature of the animal or human being, it is thermally converted to the corresponding activated vitamin D. The reaction time for thermal conversion to the active form is sufficiently long so that most of the conversion occurs over time after the 1α-hydroxyprevitamin D has been absorbed into the blood stream. Thus, the 1α-hydroxyprevitamin D oral dosage formulation produces a greater sustained blood level of the corresponding activated vitamin D with significantly less stimulation of intestinal calcium absorption than is possible with a comparable oral dosage amount of the activated vitamin D itself.

Second Embodiment

In the second embodiment of the present invention, one or more of activated vitamin D compounds are included in an enteric coated, sustained release formulation. Surprisingly, it has been found that the DSR activated D formulation of the invention significantly increases the therapeutic window of the activated vitamin D compound. That is, the risk of hypercalcemia and hypercalciuria is significantly decreased and the therapeutic effectiveness is significantly increased for the activated vitamin D when orally administered in the DSR activated D formulation as compared to the same amount of activated vitamin D orally administered in heretofore known oral formulations of those compounds. Furthermore, the DSR activated D formulation permits a higher sustained blood level of the activated vitamin D to be obtained than was possible with previously known oral formulations of the activated vitamin D compound.

The 1α-hydroxyvitamin D of this embodiment of the present invention has the general formula (III):

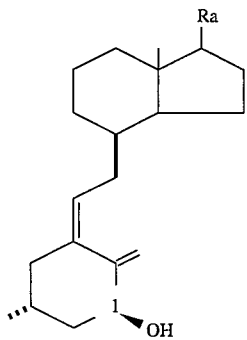

wherein $R_a$ is a side chain having at least 7 carbon atoms, and can be branched or unbranched, saturated or unsaturated, hetero-substituted or nonhetero-substituted, cyclic or noncyclic or any vitamin D compound or homologue which binds with the vitamin D receptor protein.

Among the preferred 1α-hydroxyvitamin D compounds of this embodiment of the present invention are those having the formula (IV):

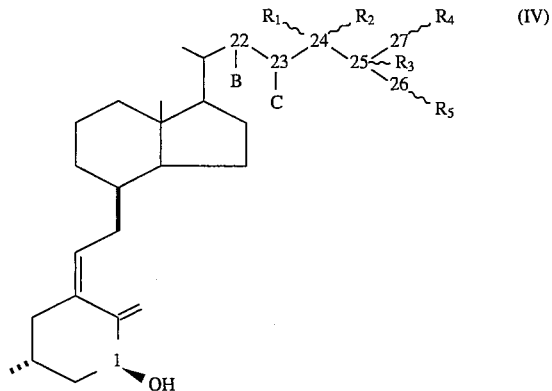

wherein B and C are either hydrogen or a carbon to carbon bond forming a double bond between C22 and C23; $R_1$, $R_3$, $R_4$ and $R_5$ are each independently hydrogen, hydroxy, lower alkyl, O-lower alkyl, O-lower acyl, O-aromatic acyl or flouro; and $R_2$ is hydrogen or lower alkyl. Most preferred among the compounds of formula (II), i.e., most preferred 1α-hydroxyvitamin D compounds, are:

1α,25-dihydroxy-cholecalciferol [1α,25-$(OH)_2D_3$];
1α,24,25-trihydroxy-cholecalciferol [1α,24,25-$(OH)_3D_3$];
1α-hydroxy-cholecalciferol[1α-$(OH)D_3$];
1α-hydroxy-25-fluoro-cholecalciferol[1α-$(OH)25FD_3$]
1α,24-dihydroxy-cholecalciferol[1α,24-$(OH)_2D_3$];
1α,24-dihydroxy-25-fluoro-cholecalciferol[1α,24-$(OH)_2$25$FD_3$];
1α,25-dihydroxy-ergocalciferol[1α,25-$(OH)_2D_2$];
1α,24,25-trihydroxy-ergocalciferol[1α,24,25-$(OH)_3D_2$];
1α-hydroxy-ergocalciferol[1α-$(OH)D_2$];
1α-hydroxy-25-fluoro-ergocalciferol[1α-$(OH)25FD_2$]
1α,24-dihydroxy-ergocalciferol[1α,24-$(OH)_2D_2$];
1α,24-dihydroxy-25-fluoro-ergocalciferol[1α,24-$(OH)_2$25$FD_2$];
1α,25-dihydroxy-vitamin $D_4$[1α,25-$(OH)_2D_4$];
1α,24,25-trihydroxy-vitamin $D_4$[1α,24,25-$(OH)_3D_4$];
1α-hydroxy-vitamin $D_4$[1α-$(OH)D_4$];
1α-hydroxy-25-fluorovitamin $D_4$[1α-$(OH)25FD_4$];
1α, 24-dihydroxy-vitamin $D_4$[1α,24-$(OH)_2D_4$]; and
1α,24-dihydroxy-25-fluoro-vitamin $D_4$1α,24-$(OH)_2$25$FD_4$].

In the formulae shown in this specification and in the claims, a wavy line to substituent X indicates that the substituent can be stereoisomeric alternate forms. Wherever in this specification and in the claims the word "lower" is used as a modifier of alkyl or acyl, it is intended to identify a hydrocarbon chain having from about 1 to 4 carbon atoms which has either a straight chain or branched chain configuration. Specific examples of such hydrocarbon chains are: methyl, ethyl, propyl, butyl, isobutyl or t-butyl, and formyl, acetyl, propionyl,or butyryl. The term "aromatic acyl" as used herein and in the claims is meant to identify a benzoyl group or a substituted benzoyl group such as nitrobenzoyl or dinitrobenzoyl.

The pharmacologically active compounds of this embodiment can be processed in accordance with conventional methods of pharmacy to produce delayed and sustained release medicinal agents (more specifically described below) for administration to patients, e.g., mammals, including human beings. For example, dosage forms of the compounds of formulas (III) and (IV) with conventional excipients, include admixtures suitable for oral administration. Dosage forms of the 1α-hydroxyvitamin D can be combined with any nontoxic pharmaceutically acceptable carrier, such as cornstarch, lactose, or sucrose, which does not deleteriously react with the active compounds. The DSR formulation can be produced in tablet or capsule form.

The preferred formulation of this embodiment is a matrix which binds the 1α,25-dihydroxyvitamin $D_3$ along with an acceptable pharmaceutical excipient and which permits a slow, relatively steady release of the 1,25-dihydroxyvitamin $D_3$ over a period of four to eight hours. The formulation further has an enteric coating that dissolves at a pH of about 6.0 to 7.0.

The means for providing sustained (i.e., controlled) release of the active ingredient may be selected from any of the known sustained-release delivery systems for controlling the release of an active ingredient over a course of about four or more hours including the wax matrix system, and the Eudragit RS/RL system (of Rohm Pharma, GmbH, Weiterstadt, Germany).

The wax matrix system disperses the active ingredient(s) in a wax binder which slowly dissolves in body fluids to gradually release the active ingredient(s).

The preferred controlled-release oral drug delivery system is the Eudragit RL/RS system in which the active ingredient, activated D, is formed into granules having a dimension of 25/30 mesh. The granules are then uniformly coated with a thin polymeric lacquer which is water insoluble but slowly water permeable. The coated granules can be mixed with optional additives such as antioxidants, stabilizers, binder, lubricant, processing aids and the like. The mixture may be compacted into a tablet which, prior to use, is hard and dry or it may be poured into a capsule. After the tablet or capsule is swallowed and comes into contact with the aqeuous intestinal fluids, the thin lacquer begins to swell and slowly allows permeation of intestinal fluids. As the intestinal fluid slowly permeates the lacquer coating, the active ingredients are slowly released. By the time the tablet has passed through the intestinal tract, about four to eight hours, the active ingredients will have been slowly but completely released. Accordingly, the ingested tablet will release a stream of the activated D as well as any other active ingredient.

The Eudragit system is comprised of high permeability lacquers (RL) and low permeability lacquers (RS). The permeability of the coating and thus the time course of drug release can be titrated by varying the proportion of RS to RL coating material.

For further details of the Eudragit RL/RS system, reference is made to technical publications available from Rohm Tech, Inc. 195 Canal Street, Maiden, Mass., 02146. See also, K. Lehmann, D. Dreher "Coating of tablets and small particles with acrylic resins by fluid bed technology", *Int. J. Pharm. Tech. & Prod. Mfr.* 2(r), 31–43 (1981).

Once the coated granuales are either formed into a tablet or put into a capsule, the tablet or capsule is coated with an enteric-coating material which dissolves at a pH of 6.0 to 7.0. One such pH dependent enteric-coating material is Eudragit L/S which dissolves in intestinal fluid but not in the gastric juices. Other enteric-coating materials may be used such as cellulose acetate phthalate (CAP) which is resistant to dissolution by gastric juices but readily disintegrates due to the hydrolytic effect of the intestinal esterases.

The particular choice of enteric-coating material and sustained or controlled release coating material is not of significance as long as a sustained or controlled release over a period of 4 to 8 hours is obtained and release is delayed until the DSR formulation reaches the intestine. Although not essential to the invention, it is preferred that release is delayed until the DSR formulation has reached beyond the proximal part of the small intestine.

The invention may also be practiced by omitting the enteric coating and using only a sustained release activated vitamin D oral formulation ("SR activated D"). While less desirable than the DSR activated D formulation, the SR activated D formulation is found to provide a wider therapeutic index than any heretofore known oral formulation of activated D. It is to be understood that the SR activated D formulation is considered to fall within the scope of the invention described and claimed herein.

Third Embodiment

The third embodiment of the invention combines the teachings of the first and second embodiments. That is, an effective amount of one or more of the 1α-previtamin D compounds of formulas (I) or (II) of the first embodiment can be contained in a delayed and sustained release formulation similar to that of the second embodiment. Alternatively, one or more of the 1α-previtamin D compounds of formulas (I) or (II) can be combined with one or more of the compounds of formulas (III) or (IV) in a delayed and sustained release formulation.

The compounds of formulas (I), (II), (III) and (IV) are useful as active compounds in the pharmaceutical compositions of the above described embodiments. Such compositions may include physiologically acceptable excipients or vehicles. These pharmaceutical compositions constitute another aspect of the invention.

The dosage forms may also contain adjuvants, such as preserving or stabilizing adjuvants. They may also contain other therapeutically valuable substances or may contain more than one of the compounds specified herein and in the claims in admixture.

Advantageously, the compounds of formulas (I), (II), (III) and (IV) or combinations thereof together with other therapeutic agents can be orally administered in accordance with the above described embodiments in dosage amounts of from 0.1 to 100 micrograms per day. In relation to osteoporosis, doses from about 0.5 to about 25 micrograms per day are generally effective. If the compounds of the present invention are administered in combination with other therapeutic agents, the proportions of each of the compounds in the combination being administered will be dependent on the particular disease state being addressed. For example, in the case of osteoporosis, one may choose to administer the previtamin form of the activated vitamin D or the activated vitamin D compound with an estrogen compound, Calcitriol, Calcitonin or a bisphosphonate. In practice, higher doses of the compounds of the present invention are used where therapeutic treatment of a disease state is the desired end, while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

While the preferred embodiments are described above, it should be understood that the only limitation as to the kind of active vitamin D compound used in this invention is that the vitamin D compound binds with the vitamin D receptor protein.

The embodiments of the present invention are further explained by the following examples which should not be construed by way of limiting the scope of the present invention. In the following examples, high pressure liquid chromatography (HPLC) was performed on a Waters Instrument, using a Zorbax Sil ODS column.

EXAMPLE 1

Time Course of 1α-hydroxyprevitamin D Conversion to 1α-hydroxyvitamin D

One and a half micrograms of 1α-hydroxyvitamin $D_2$ was dissolved in 2.00 ml ethanol. This solution was then subjected to a 60° C. water bath for 24 hours. Fractions of 1α-hydroxyprevitamin $D_2$ [1α-OH-pre-$D_2$] were collected in nearly pure amounts from this treated sample. These previtamin fractions were pooled in a single test tube, dried under nitrogen gas on ice and eventually redissolved in 1.00 ml ethanol. The pooled fraction of previtamin, upon HPLC analysis, indicated 96% was previtamin at t=0 time.

A tube with the pooled previtamin was then placed in a 37° C. water bath. 50 µl aliquots were removed and placed into LVI tubes with a cold water jacket around them. Samples were chromatographed to determine the percent of 1α-hydroxyprevitamin $D_2$ and 1α-OH-$D_2$ present in each sample. Sampling times were 0, 0.5, 1.0, 1.5, 2.0, 2.5, 3.0, 3.5, 4.0, 6.0, and 8.0 hours. Results are presented below in Tables 1 and 2:

TABLE 1

1α-OH-$D_2$ SAMPLE PREPARATION

| SAMPLE | % PREVITAMIN | % 1α-OH-$D_2$ |
| --- | --- | --- |
| Starting Material | 0.00 | 99 |
| 24 hours at 60° C. | 8 | 92 |
| Pooled Fractions | 96 | 4 |

TABLE 2

TIME COURSE OF 1α-OH PREVIAMIN $D_2$

| SAMPLE (T = hrs) | % 1α-OH-PRE-$D_2$ | % 1α-OH-$D_2$ |
| --- | --- | --- |
| T = 0.0 | 96 | 4 |
| T = 0.5 | 93 | 7 |
| T = 1.0 | 90 | 10 |
| T = 1.5 | 86 | 13 |
| T = 2.0 | 83 | 17 |
| T = 2.5 | 79 | 21 |
| T = 3.0 | 77 | 23 |
| T = 3.5 | 73 | 27 |
| T = 4.0 | 71 | 29 |
| T = 6.0 | 61 | 39 |
| T = 8.0 | 52 | 48 |

These results indicate that at normal body temperature, a 50% conversion of 1α-hydroxyprevitamin $D_2$ to 1α-hydroxyvitamin $D_2$ in vitro required approximately eight hours. In vivo one would expect a similar rate of conversion. These data indicate that thermal conversion at normal body temperature is sufficiently slow that most of the 1α-hydroxyprevitamin D compound is absorbed into the blood stream in the previtamin form and conversion to the activated vitamin D counterpart occurs principally after absorption from the intestine. This results in a greater sustained blood level of activated vitamin D with less stimulation of intestinal calcium absorption than is seen with administering the corresponding activated vitamin D compound orally.

EXAMPLE 2

In Vitro Biological Activity

1α,25-dihydroxyprevitamin $D_3$ or 1α,25-dihydroxyvitamin $D_3$ were incubated with the vitamin D receptor protein and tracer amounts of $^3$H-1α,25-(OH)$_2$D$_3$ under standard conditions for a competitive binding assay. The amount of 1α,25-dihydroxyprevitamin $D_3$ and 1α,25-dihydroxyvitamin $D_3$ competitor was varied between 7.8 and 1000 pg or 1.0 and 25 pg, respectively.

Concurrent with the incubations for binding, a tube of 1α,25-dihydroxyprevitamin $D_3$ was incubated at the same temperature and for the same length of time to assess the amount of 1α,25-dihydroxyprevitamin $D_3$ that had equilibrated to the vitamin form. HPLC analysis indicated that at the end of the incubation period approximately 2% of the 1α,25-dihydroxyprevitamin $D_3$ had equilibrated to the vitamin form. The level of binding of the 1α,25-dihydroxyprevitamin $D_3$ form was corrected for the amount of the vitamin form that had been generated during the assay procedure.

TABLE 3

Binding of 1α,25-dihydroxyprevitamin $D_3$ to vitamin D Receptor in vitro

| Amount 1,25-pre$D_3$ (pg/tube) | Total Detectable Binding (pg/tube) | Corrected Binding (pg/tube) |
| --- | --- | --- |
| 7.8 | ND | ND |
| 15.6 | ND | ND |
| 31.3 | ND | ND |
| 62.5 | 1.88 | 0.6 |
| 125 | 3.02 | 0.5 |
| 250 | 6.32 | 1.3 |
| 500 | 12.0 | 2.0 |
| 1000 | 20.5 | 0.5 |

The data shown in Table 3 above show that the 1α,25-dihydroxyprevitamin $D_3$ form has an affinity for the receptor less than 0.01 the affinity of the 1α,25-dihydroxyvitamin $D_3$ form, thus 1α,25-dihydroxyprevitamin $D_3$ must equilibrate to the 1α,25-dihydroxyvitamin $D_3$ form before it is biologically active.

EXAMPLE 3

Acute Hypercalcemia Testing

Male weanling rats are fed a vitamin D deficient diet containing normal Ca (0.47%) and P (0.3%). After approximately 4–6 weeks on this diet, the rats are separated into five groups and orally administered either 1α,25-dihydroxyvitamin $D_3$ (0.06 or 0.12 ug/kg/day) or 1α,25-dihydroxyprevitamin $D_3$ (0.06 or 0.12 ug/kg/day) in a vehicle such as lactose, or the vehicle alone (control), for 3 days. All animals are exsanguinated 24 hours after the last dose and the blood is analyzed for serum calcium and serum phosphorus. The results demonstrate that dosing with 1α,25-dihydroxyvitamin $D_3$ causes a greater rise in serum calcium and serum phosphorus than comparable dosing with 1α,25-dihydroxyprevitamin $D_3$.

EXAMPLE 4

Bioavailability Testing

Male weanling rats are fed a diet deficient in vitamin D and with normal calcium (0.47%). After a period of four weeks has elapsed, the rats are divided into two groups, and orally administered either 1α,25-dihydroxyprevitamin $D_3$ (0.25 μg/kg) in a vehicle such as lactose or the vehicle (control) alone. Four hours after administration, the rats are killed and their blood level of 1α,25-dihydroxyvitamin $D_3$ is measured using a standard technique.

Following this procedure demonstrates that the blood level of 1α,25-dihydroxyvitamin $D_3$ in rats that are administered 1α,25-dihydroxyprevitamin $D_3$ is significantly elevated over the blood level of control animals.

EXAMPLE 5

In Vivo Biological Activity Testing

Male weanling rats were fed a vitamin D deficient diet containing normal Ca (0.47%) and P (0.3%). After three weeks on this diet, the rats were separated into four groups and orally administered 0.042, 0,250, or 1.50 μg/kg 1α,25-dihydroxyprevitamin $D_3$ in a cold vehicle or the cold vehicle alone (control) for each of 14 days. Twenty-four hours after the last dose, the rats were killed and the blood calcium and 1α,25-dihydroxyvitamin $D_3$ levels are measured. The blood calcium levels shown in the table below demonstrated that the serum calcium level was higher in the 1α,25-dihydroxyprevitamin $D_3$ dosed animals than in the control animals, indicating that ultimately 1α,25-dihydroxyprevitamin $D_3$ possesses biological activity.

TABLE 4

Increase in Serum Calcium After
1α,25-dihydroxyvitamin $D_3$ Administration

| Compound | Dose (μg/kg/d) | Serum Calcium (mg/dl ± SD) |
| --- | --- | --- |
| Vehicle | — | 6.0 ± 0.47 |
| 1,25-preD$_3$ | 0.042 | 7.8 ± 1.02 |
| | 0.250 | 9.6 ± 1.48 |
| | 1.500 | 11.4 ± 0.61 |

This procedure also demonstrates that the serum 1α,25-dihydroxyvitamin $D_3$ levels are higher in the 1α,25-dihydroxyprevitamin $D_3$ dosed animals than in the control animals.

EXAMPLE 6

Pharmacokinetics Testing

Male weanling rats are fed a vitamin D deficient diet containing normal Ca (0.47%) and P (0.3%). After four weeks on this diet, the rats are separated into seventeen groups and orally administered either 1α,25-dihydroxyvitamin $D_3$ or 1α,25-dihydroxyprevitamin $D_3$ in a vehicle such as lactose or the vehicle alone (control). One group is killed 8 hours after dosing with the vehicle. Eight groups are orally administered a single dose of either 1α,25-dihydroxyprevitamin $D_3$ or 1α,25-dihydroxyvitamin $D_3$ and killed at 2, 4, 6, 9, 12, 18, 24, and 48 hours after dosing. The blood is collected and analyzed for 1α,25-dihydroxyvitamin $D_3$ levels.

The results demonstrate that dosing with 1α,25-dihydroxyprevitamin $D_3$ results in increased 1α,25-dihydroxyvitamin $D_3$ serum levels. The results further demonstrate that the increase in serum 1α,25-dihydroxyvitamin $D_3$ is more gradual and sustained for a greater duration than the 1α,25-dihydroxyvitamin $D_3$ pharmacokinetics observed after dosing with 1α,25-dihydroxyvitamin $D_3$.

EXAMPLE 7

Treatment of Osteoporosis

A clinical study is conducted with postmenopausal osteoporotic outpatients having ages between 55 and 75 years. The study involves up to 120 patients randomly divided into three treatment groups, and continues for 24 months. Two of the treatment groups receive constant dosages of orally administered 1α,25-dihydroxyprevitamin $D_3$ (u.i.d.; two different dose levels above 0.5 μg/day) and the other group receives a matching placebo. All patients maintain a normal intake of dietary calcium (500 to 800 mg/day) and refrain from using calcium supplements. Efficacy is evaluated by pretreatment and posttreatment comparisons of the patient groups with regard to (a) total body, radial, femoral, and/or spinal bone mineral density as determined by x-ray absorptiometry (DEXA), (b) bone biopsies of the iliac crest, and (c) determinations of serum osteocalcin. Safety is evaluated by comparisons of urinary hydroxyproline excretion, serum and urine calcium levels, creatinine clearance, blood urea nitrogen, and other routine determinations.

This study demonstrates that patients treated with orally administered 1α,25-dihydroxyprevitamin $D_3$ exhibit significantly higher total body, radial, femoral, and/or spinal bone densities relative to patients treated with placebo. The treated patients also exhibit significant elevations in serum osteocalcin. Bone biopsies from the treated patients show that 1α,25-dihydroxyprevitamin $D_3$ stimulates normal bone formation. The monitored safety parameters confirm an insignificant incidence of hypercalcemia or hypercalciuria, or any other metabolic disturbance with 1α,25-dihydroxyprevitamin $D_3$.

EXAMPLE 8

Prevention of Osteoporosis

A clinical study is conducted with healthy postmenopausal women having ages between 55 and 60 years. The study involves up to 80 patients randomly divided into two treatment groups, and continues for 12 to 24 months. One treatment group receives a constant dosage of 1α,25-dihydroxyprevitamin $D_3$ (u.i.d.; a dose level above 0.5 μg/day) and the other receives a matching placebo. The study is conducted as indicated in Example 6 above.

This study demonstrates that patients treated with 1α,25-dihydroxyprevitamin $D_3$ exhibit reduced losses in total body, radial, femoral, and/or spinal bone densities relative to baseline values. In contrast, patients treated with placebo show significant losses in these parameters relative to baseline values. The monitored safety parameters confirm the safety of long-term 1α,25-dihydroxyprevitamin $D_3$ administration at this dose level.

EXAMPLE 9

Prevention of Hypocalcemia and Bone Loss in Renal Dialysis Patients

A 12-month double-blind placebo-controlled clinical trial is conducted with 30 men and/or women with renal disease who are undergoing chronic hemodialysis. All patients enter an 8-week control period during which time they receive a maintenance dose of vitamin $D_3$ (400 IU/day). After this control period, the patients are randomized into two treatment groups: one group receives a constant dosage of $1\alpha,25$-dihydroxyprevitamin $D_4$ (u.i.d., a dosage greater than 3.0 µg/day), and the other group receives a matching placebo. Both treatment groups receive a maintenance dosage of vitamin $D_3$, maintain a normal intake of dietary calcium, and refrain from using calcium supplements. Efficacy is evaluated by pretreatment and posttreatment comparisons of the two patient groups with regard to (a) direct measurements of intestinal calcium absorption, (b) total body, radial, femoral, and/or spinal bone mineral density, and (c) determinations of serum calcium and osteocalcin. Safety is evaluated by regular monitoring of serum calcium.

Analysis of the clinical data shows that $1\alpha,25$-dihydroxyprevitamin $D_4$ significantly increases serum osteocalcin levels and intestinal calcium absorption, as determined by measurements using a single- or double-isotope technique. Patients treated with this compound show normalized serum calcium levels, stable values for total body, radial, femoral, and/or spinal bone densities relative to baseline values. In contrast, patients treated with placebo show frequent hypocalcemia, significant reductions in total body, radial, femoral, and/or spinal bone density. An insignificant incidence of hypercalcemia is observed in the treated group.

EXAMPLE 10

Treatment of Psoriasis

An oral dosage formulation containing $1\alpha,24$-dihydroxyprevitamin $D_2$ is evaluated in a double blind study for therapeutic efficacy of the formulation in the treatment of dermatitis (contact and ectopic). The formulation evaluated contains 1.0 to 2.0 µg of $1\alpha,24$-dihydroxyprevitamin $D_2$. The control formulation is identical except that it does not contain the $1\alpha,24$-dihydroxyprevitamin $D_2$. The patients are treated in an outpatient clinic and are divided into an experimental and control population. They are instructed to take the medication once a day, in the morning before breakfast.

In each patient (experimental and control) an area of the skin containing a lesion is selected which is ordinarily covered by clothing and the patients are instructed not to expose the skin area selected for study to sunlight. The area of the lesion is estimated and recorded, and the lesion(s) is photographed. Relevant details of the photographic procedure are recorded so as to be reproduced when the lesions are next photographed (distance, aperture, angle, background, etc.).

Evaluations of erythema, scaling, and thickness are conducted at weekly intervals by a physician. The final evaluation is usually carried out at the end of four to six weeks of treatment. The results of the study show that daily oral administration of $1\alpha,24$-dihydroxyprevitamin $D_2$ significantly reduces the degree of erythema, scaling, and thickness versus the control patients.

EXAMPLE 11

Formulation with Equal Parts Eudragit L100 and S100

An appropriate amount of activated vitamin D was dissolved in ethanol and combined with the matrix components listed in Table 5 and sprayed onto 850 g 25/30 mesh nonpariel beads. After drying, the beads were coated with the enteric coat listed in Table 5.

TABLE 5

| Component | Ingredient | Amount (g) |
| --- | --- | --- |
| Matrix | Eudragit RS100 | 50 |
|  | Methanol | 50 |
|  | Ethanol with drug |  |
|  | Distilled water | 5 |
|  | Acetone | qs to 500 |
| Enteric coat | ATEC (acetyl triethyl citrate, a plasticizer) | 54 |
|  | Methanol | 600 |
|  | Distilled water | 30 |
|  | Eudragit L100 | 153 |
|  | Eudragit S100 | 153 |
|  | Talc | 40 |
|  | Acetone | qs to 4000 |

After formulation the beads (500 mg/capsule) are packaged in #0 gelatin capsules for administration to dogs.

Dogs (Beagles, males and females, 13 kg and 9 kg, respectively) were administered 5 capsules/day of formulation. Blood is drawn for baseline determination, 24 hours after dosing but prior to subsequent dosing, and the serum calcium determined. Dose administration is terminated after 2 days with serum calcium levels significantly above normal.

Five capsules/day of the above formulation (DSR-008) were administered to a female dog for 7 days. The normal serum calcium range in female dogs is 10.0 to 12.4 mg/dl with a mean of 11.2 mg/dl. The serum calcium at baseline of this experiment was 11.7 mg/dl; the subsequent values on successive days were as follows: 12.1, 12.3, 12.7, 13.1, 13.5, and 15.1 mg/dL.

These results show that the biological activity of the drug in this formulation is revealed over a sustained period.

EXAMPLE 12

Formulation with Unequal Amounts Eudragit L100 and S90.

An appropriate amount of activated vitamin D was dissolved in ethanol and combined with the matrix components listed in Table 6 and sprayed onto 850 g 25/30 mesh non-pariel beads. After drying, the beads were coated with the enteric coat listed in Table 6.

TABLE 6

| Component | Ingredient | Amount (g) |
| --- | --- | --- |
| Matrix | Eudragit RS100 | 10 |
|  | Methanol | 10 |
|  | Ethanol with drug |  |
|  | Distilled water | 1 |
|  | Acetone | qs to 100 |
| Enteric coat | ATEC (acetyl triethyl citrate, a plasticizer) | 68 |
|  | Methanol | 750 |
|  | Distilled water | 35 |
|  | Eudragit L100 | 338 |
|  | Eudragit S90 | 49 |
|  | Talc | 50 |
|  | Acetone | qs to 5000 |

After formulation the beads (500 mg/capsule) are packaged in #0 gelatin capsules for administration to dogs.

Dogs (as in Example 11) were administered 5 capsules/day of formulation. Blood is drawn for baseline determination, 24 hours after dosing but prior to subsequent dosing, and the serum calcium determined. Dose administration is terminated after 2 days with serum calcium levels significantly above normal.

Five capsules/day of the above formulation (DSR-010) were administered to a female dog for 2 days. The normal serum calcium range in female dogs is 10.0 to 12.4 mg/dl with a mean of 11.2 mg/dl. The serum calcium at baseline was 10.9; the subsequent values on successive days were as follows: 13.8 and 16.1 mg/dl.

These data show that the drug in this delayed release formulation is readily bioavailable.

EXAMPLE 13

Formulation with Stearic Acid Matrix

An appropriate amount of activated vitamin D was dissolved in ethanol and combined with the matrix components listed in Table 7 and sprayed onto 850 g 25/30 mesh nonpariel beads. After drying, the beads were coated with the enteric coating listed in Table 7.

TABLE 7

| Component | Ingredient | Amount (g) |
|---|---|---|
| Matrix | Stearic acid | 10 |
| | Ethanol with drug | |
| | Acetone | qs to 90 |
| Enteric coat | ATEC (acetyl triethyl citrate, a plasticizer) | 68 |
| | Methanol | 750 |
| | Distilled water | 35 |
| | Eudragit L100 | 338 |
| | Eudragit S90 | 49 |
| | Talc | 50 |
| | Acetone | qs to 5000 |

After formulation the beads (500 mg/capsule) are packaged in #0 gelatin capsules for administration to dogs.

Dogs (as in Example 11) were administered 5 capsules/day of formulation. Blood is drawn for baseline determination, 24 hours after dosing but prior to subsequent dosing, and the serum calcium determined. Dose administration is terminated after 2 days with serum calcium levels significantly above normal.

Five capsules/day of the above formulation (DSR-012) were administered to a male dog for 2 days. The normal serum calcium range in male dogs at this facility is 10.6 to 12.0 mg/dl with a mean of 11.3 mg/dl. The serum calcium at baseline was 11.4 mg/dl; the subsequent values on successive days were as follows: 14.2 and 15.5 mg/dl.

These data illustrate that drug in this formulation is readily bioavailable in this delayed release formulation.

EXAMPLE 14

Pharmacokinetics Testing

A dog receives a capsule of $1\alpha,25$-dihydroxyvitamin $D_3$ drug formulated as illustrated in this invention (DSR). Another dog receives a similar amount of the $1\alpha,25$-dihdyroxyvitamin $D_3$ in fractionated coconut oil. Blood is drawn at 0, 0.5, 1, 1.5, 2, 3, 4, 6, 9, 15, 24, 36, and 72 hours after dose administration. The blood is analyzed for active vitamin D levels. The animal administered the drug in the capsule formulation shows a slower rise in blood concentration of active vitamin D, a lower maximum concentration of active vitamin D in the blood and prolonged elevation of active vitamin D blood level relative to the animal receiving the drug in fractionated coconut oil (FCO).

FIG. 1 depicts the blood levels of active vitamin D expected from the above example.

These procedures demonstrate that dosing animals with the formulation described in this invention results in $1\alpha,25$-dihydroxyvitamin $D_3$ serum levels with a slower rise and longer duration than the $1\alpha,25$-dihydroxyvitamin $D_3$ pharmacokinetics observed after dosing with $1\alpha,25$-dihydroxyvitamin $D_3$ in fractionated coconut oil.

EXAMPLE 15

Delayed and Sustained Levels of Active Vitamin D in Serum

Patients are administered two micrograms of calcitriol formulated as described in this invention. Blood samples collected 0, 2, 6, 8, and 12 hours after dose administration are analyzed for calcitriol levels. The results indicate that the levels of calcitriol at 2, 6, and 8 hours are increased over the level at 0, but are below levels considered hypercalcemic. These results indicate a delayed and sustained release of calcitriol.

EXAMPLE 16

Lack of Toxic Responses to Active Vitamin Formulation

Patients are administered 2.0 micrograms of calcitriol formulated as described in this invention once daily for 7 days. An overnight urine collection after the last dose, and blood drawn 24 hours after the last dose are analyzed for calcium content. No hypercalcemia or hypercalciuria is observed, indicating low toxicity.

EXAMPLE 17

Treatment of Osteoporosis

Postmenopausal osteoporotic women are administered 1.0 microgram of calcitriol formulated as described in this invention once daily for 2 years or placebo. The drug was well tolerated by the women and at the conclusion of the two years, bone mineral density was significantly greater in the women administered drug, and the rate of fractures was less in women administered the drug as compared to those administered placebo.

EXAMPLE 18

Treatment of Psoriasis

A formulation of calcitriol as described in this invention is evaluated in a double blind study for therapeutic efficacy of the formulation in the treatment of dermatitis (contact and ectopic). The formulation evaluated contains 0.5 to 2.0 μg of calcitriol. The control formulation is identical except that it does not contain the calcitriol. The patients are treated in an outpatient clinic and are divided into an experimental and control population. They are instructed to take the medication once a day.

In each patient (experimental and control) an area of the skin containing a lesion is selected which is ordinarily covered by clothing and the patients are instructed not to expose the skin area selected for study to sunlight. The area of the lesion is estimated and recorded, and the lesion(s) is photographed. Relevant details of the photographic procedure are recorded so as to be reproduced when the lesion(s) are next photographed (distance, aperture, angle, background, etc.)

Evaluations of erythema, scaling, and thickness are conducted at weekly intervals by a physician. The final evaluation is usually carried out at the end of four to six weeks of treatment. The results of the study show that daily oral administration of calcitriol in this formulation does not produce clinicaly significant hypercalcemia or hypercalciuria and significantly reduces the degree of erythema, scaling, and thickness versus the control patients.

In summary, the present invention provides methods for ameliorating certain medical conditions by improving blood levels of activated vitamin D. The improved levels are achieved by administration of an oral formulation of 1α-hydroxyprevitamin D or DSR activated vitamin D or combination thereof. The formulations of the invention significantly reduce the risk of hypercalcemia and hypercalciuria associated with heretofore known formulations of activated vitamin D. Furthermore, the formulation of the invention produces higher levels of activated vitamin D for a greater sustained time per administration than is obtained with heretofore known oral formulations of activated vitamin D.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. An oral medicament for use in a human having a stomach and intestine, said oral medicament comprising: a matrix containing a vitamin D compound which is activated vitamin D or 1α-hydroxyvitamin D in unit dosage amount, said matrix having means for releasably binding said vitamin D compound and means for controlled release of said vitamin D compound over a sustained period of time.

2. An oral medicament as described in claim 1, further comprising: an enteric coating which covers said matrix and prevents release of said vitamin D compound, said enteric coating being resistant to dissolution in said stomach but predisposed to dissolution in the environment of said intestine so as to prevent release of said vitamin D compound from said matrix until said medicament is in said intestine.

3. An oral medicament for use in a human having a gastrointestinal tract including a stomach and small intestine, said small intestine having a proximal, middle and distal portion, said oral medicament comprising: an enteric coating and a matrix containing a vitamin D compound which is activated vitamin D or 1α-hydroxyprevitamin D in unit dosage amount, said matrix having means for releasably binding said vitamin D compound and means for controlled release of said vitamin D compound over a sustained period of time when exposed to the environment of said gastrointestinal tract, said enteric coating covering said matrix and preventing release of said vitamin D compound from said matrix, said enteric coating being resistant to dissolution in said stomach but predisposed to dissolution in the environment of said intestine so as to prevent release of said vitamin D compound from said matrix until said medicament is in said intestine.

4. An oral medicament as claimed in claim 3, wherein said enteric coating is further resistant to dissolution in the proximal portion of said small intestine but predisposed to dissolution in the middle and distal portion of said small intestine so as to prevent release of said vitamin D compound from said matrix until said medicament has traveled to the middle portion of said small intestine.

5. An oral medicament for use in a human having a stomach and small intestine, said small intestine having a proximal, middle and distal portion, and said human displaying or predisposed to loss of bone mass, said medicament, comprising: a matrix containing 1α,25-dihydroxy vitamin $D_3$ in unit dosage form and an enteric coating covering said matrix, said enteric coating being resistant to dissolution in an environment having a pH less than 6.0 but predisposed to dissolution in an environment having a pH above 6.0, said matrix having a means for releasably binding said 1α,25-dihydroxy vitamin $D_3$ and means for controlled release of said 1α,25-dihydroxy vitamin $D_3$ when said enteric coating is dissolved and said matrix is exposed to the environment of said intestine.

6. A method for treating or preventing loss of bone mass or bone mineral content in a human displaying or predisposed to osteoporosis, said human having a stomach and intestine, said method comprising: the step of administering orally to said human an oral medicament comprising a matrix containing a vitamin D compound which is activated vitamin D or 1α-hydroxyprevitamin D, said matrix having means for releasably binding said vitamin D compound and means for controlled release of said vitamin D compound over a sustained period of time.

7. A method for treating or preventing loss of bone mass as claimed in claim 6, wherein said oral medicament further comprises an enteric coating which covers said matrix and prevents release of said vitamin D compound, said enteric coating being resistant to dissolution in said stomach but predisposed to dissolution in the environment of said intestine so as to prevent release of said vitamin D compound from said matrix until said medicament is in said intestine.

8. A method for treating or preventing loss of bone mass as claimed in claim 6, wherein said activated vitamin D is 1α,25 dihydroxy vitamin $D_3$.

9. A method for treating or preventing psoriasis in a human displaying or predisposed to psoriasis, said method comprising: the step of administering orally to said human being an oral medicament comprising a matrix containing a vitamin D compound which is activated vitamin D or 1α-hydroxyprevitamin D, said matrix having means for releasably binding said vitamin D compound and means for controlled release of said vitamin D compound over a sustained period of time.

10. A method for treating psoriasis as claimed in claim 9, wherein said oral medicament further comprises an enteric coating which covers said matrix and prevents release of said vitamin D compound, said enteric coating being resistant to dissolution in said stomach but predisposed to dissolution in the environment of said intestine so as to prevent release of said vitamin D compound from said matrix until said medicament is in said intestine.

11. A method for treating psoriasis as claimed in claim 9, wherein said activated vitamin D is 1α,25-dihydroxyvitamin $D_3$.

12. An oral medicament as claimed in claim 2, wherein said enteric coating is resistant to dissolution in an environment having a pH less than 6.0.

13. An oral medicament as claimed in claim 3, wherein said enteric coating is resistant to dissolution in an environment having a pH less than 6.0.

14. An oral medicament as claimed in claim 2, wherein said enteric coating is a cellulose, acetate-like polymer.

15. An oral medicament as claimed in claim 3, wherein said enteric coating is a cellulose, acetate-like polymer.

16. An oral medicament as claimed in claim 1, wherein said activated vitamin D is 1α,25-dihydroxy vitamin $D_3$.

17. An oral medicament as claimed in claim 2, wherein said activated vitamin D is 1α,25-dihydroxy vitamin $D_3$.

18. An oral medicament as claimed in claim 3, wherein said activated vitamin D is 1α,25-dihydroxy vitamin $D_3$.

19. An oral medicament as claimed in claim 1, wherein said activated vitamin D is 1α-hydroxyvitamin D.

20. A composition comprising an oral active vitamin D medicament suitable for use in a human, and having enhanced bioavailability to provide higher sustained blood levels of activated vitamin D, said medicament comprising:

a vitamin D compound which is 1α-hydroxyvitamin D or 1α-hydroxyprevitamin D; and a matrix charged with said vitamin D compound, said matrix releasably binding and controllably releasing said vitamin D compound over a sustained period of time.

21. The composition of claim 20, wherein said sustained period of time is four to eight hours.

22. The composition of claim 20, further comprising an enteric coating surrounding said matrix charged with said vitamin D compound, said enteric coating predisposed to dissolution at a pH of about 6.0 to 7.0.

* * * * *

UNITED STATES PATENT AND TRADEMARK OFFICE
CERTIFICATE OF CORRECTION

PATENT NO. : 5,529,991
DATED : June 25, 1996
INVENTOR(S) : Joyce C. Knutson et al.

It is certified that error appears in the above-indentified patent and that said Letters Patent is hereby corrected as shown below:

Column 19, claim 1, line 37, "1α-hydroxyvitamin D" should read --1α-hydroxyprevitamin D--.

Signed and Sealed this

Twenty-fifth Day of March, 1997

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.   : 5,529,991                                    Page 1 of 2
DATED        : June 25, 1996
INVENTOR(S)  : Joyce C. Knutson et al.

It is certified that error appears in the above-identified patent and that said Letters Patent is hereby corrected as shown below:

Column 7,
Figure III, "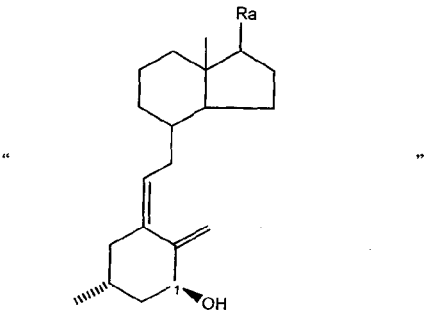"

should be replaced with -- 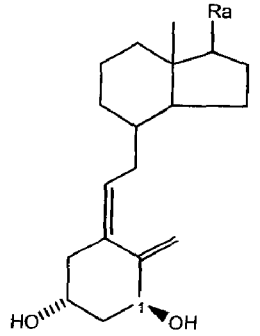 --

UNITED STATES PATENT AND TRADEMARK OFFICE
CERTIFICATE OF CORRECTION

PATENT NO.    : 5,529,991
DATED         : June 25, 1996
INVENTOR(S)   : Joyce C. Knutson et al.

It is certified that error appears in the above-identified patent and that said Letters Patent is hereby corrected as shown below:

Column 8,
Figure IV, " " should be replaced with --  --

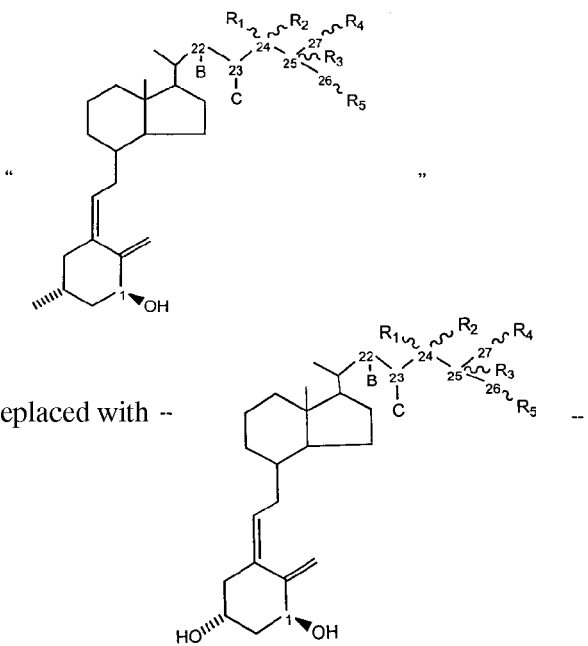

Signed and Sealed this

Twenty-second Day of March, 2005

JON W. DUDAS
*Director of the United States Patent and Trademark Office*